United States Patent
Schreiber et al.

(10) Patent No.: US 9,426,990 B2
(45) Date of Patent: Aug. 30, 2016

(54) HERBICIDAL AGENTS CONTAINING ACLONIFEN

(71) Applicant: BAYER CROPSCIENCE AG, Monheim (DE)

(72) Inventors: Dominique Schreiber, Anche (FR); Thomas Wilde, Weilrod-Hasselbach (DE); Dirk Brueggemann, Osten (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/652,166

(22) PCT Filed: Dec. 16, 2013

(86) PCT No.: PCT/EP2013/076737
§ 371 (c)(1),
(2) Date: Jun. 15, 2015

(87) PCT Pub. No.: WO2014/095745
PCT Pub. Date: Jun. 26, 2014

(65) Prior Publication Data
US 2015/0335018 A1   Nov. 26, 2015

(30) Foreign Application Priority Data
Dec. 18, 2012 (DE) .................. 10 2012 223 510

(51) Int. Cl.
*A01N 43/40* (2006.01)
*A01N 33/18* (2006.01)
*A01N 33/22* (2006.01)

(52) U.S. Cl.
CPC ............. *A01N 43/40* (2013.01); *A01N 33/18* (2013.01); *A01N 33/22* (2013.01)

(58) Field of Classification Search
None
See application file for complete search history.

(56) References Cited

U.S. PATENT DOCUMENTS

| | | | |
|---|---|---|---|
| 4,394,159 A | 7/1983 | Buck et al. | |
| 5,858,920 A * | 1/1999 | Dahmen | A01N 43/82 504/103 |
| 6,046,133 A | 4/2000 | Hewett et al. | |

FOREIGN PATENT DOCUMENTS

| | | |
|---|---|---|
| AU | 635599 B2 | 3/1993 |
| AU | 641500 B2 | 9/1993 |
| AU | 642986 B2 | 11/1993 |
| AU | 659028 B2 | 5/1995 |
| AU | 663028 B2 | 9/1995 |
| AU | 712501 B2 | 11/1999 |
| EP | 0007482 A1 | 2/1980 |
| EP | 0958742 A1 | 11/1999 |
| FR | 2611437 A1 | 9/1988 |
| FR | 2656984 A1 | 7/1991 |

OTHER PUBLICATIONS

Bond et al.(Weed Control in Carrots and Salad Onions Under Low-Level Polyethylene Covers, Brighton Crop Protection Conference, Weeds, 1989).*
Flight BASF 1999.*
International Search Report from corresponding PCT/EP2013/076737, mailed Apr. 10, 2014.
Bond et al., "Weed Control in Carrots and Salad Onions Under Low-Level Polyethylene Covers", Brighton Crop Protection Conference, Weeds, Nov. 20, 1989, England, pp. 1021-1026, XP009175639.

* cited by examiner

*Primary Examiner* — Alton Pryor
(74) *Attorney, Agent, or Firm* — McBee Moore Woodward & Vanik, LLC

(57) ABSTRACT

Herbicidal agents containing aclonifen. Herbicidal compositions having an effective amount of aclonifen and the other herbicides pendimethalin and picolinafen. These herbicidal compositions have an improved application profile.

16 Claims, No Drawings

HERBICIDAL AGENTS CONTAINING ACLONIFEN

CROSS REFERENCE TO RELATED APPLICATIONS

This application is a §371 National Stage Application of PCT/EP2013/076737, filed 16 Dec. 2013, which claims priority to DE 12012223510.8, filed 18 Dec. 2012.

BACKGROUND

1. Field of the Invention

The invention is in the technical field of the crop protection agents which can be used against harmful plants, for example in crop plants, and which, as active compounds in the herbicidal compositions, comprise a combination of aclonifen and a further herbicide.

2. Description of Related Art

The herbicidally active compound aclonifen (manufacturer: Bayer CropScience) belongs to the group of the diphenyl ethers, and mixtures of this group with other herbicides are known from the literature: for example (e.g.) U.S. Pat. No. 4,394,159 A, EP 0007482 A. U.S. Pat. No. 5,858,920 B describes, inter alia, heteroaryloxyacetamides in mixture with individual active compounds such as, for example, the herbicide aclonifen; however, without any experimental data for the synergistic effect.

The herbicidal active compound aclonifen is characterized by a broad activity against mono- and dicotyledonous harmful plants and is employed, for example, predominantly by the pre-emergence method in sown and/or planted agricultural or horticultural crop plants and also on non-crop land (for example in cereals such as wheat, barley, rye, oats, triticale, rice, corn, millet, sugar beet, sugar cane, oilseed rape, cotton, sunflowers, soybeans, potatoes, tomatoes, beans, flax, pasture grass, fruit plantations, plantation crops, greens and lawns and also squares of residential areas or industrial sites, rail tracks).

As individual active compound, aclonifen is commercially available, for example, under the trade names Challenge®, Bandur®, Fenix® and Prodigio®. In addition to the use of the individual compound, mixtures of aclonifen with other herbicides are also known from the literature (e.g. AU 635599 B, AU 642986 B, AU 641500 B, AU 659028 B, AU 663028 B, AU 712501 B, U.S. Pat. No. 6,046,133 B, EP 0958742 A) and commercially available: mixtures with amitrole (e.g. Derby®, Illico TL Express®, Muleta®), with isoxaflutole (e.g. Acajou®, Lagon®, Merlin Combi®), with alachlor (e.g. Manager®), with flurtamone (e.g. Nikeyl®), with oxadiargyl (e.g. Opalo®, Carioca®) and with oxadiazon (e.g. Phare®, Cline®).

In spite of the good activity of aclonifen as individual active compound and in the mixtures already known, there is still a need for improving the application profile of this active compound in specific areas of use. There are various reasons for this, such as, for example, further increase of efficacy in specific areas of application and in connection with different soil properties and irrigation conditions, enhancement of crop plant compatibility, as a reaction to novel production techniques in individual crops and/or to the increasing occurrence of herbicide-resistant harmful plants (e.g. in cereals, rice and corn, but also in potatoes, sunflowers, peas, carrots and fennel), for example with target-site resistance (e.g. TSR (abbreviation: TSR; where the weed populations comprise biotypes having a target-site-specific resistance, i.e. the binding site at the site of action is modified as a result of natural mutations in the gene sequence so that the active compounds are no longer able to bind, or bind in an unsatisfactory manner, and are therefore no longer able to act) and enhanced metabolic resistance (abbreviation: EMR; where the weed populations comprise biotypes having a metabolic resistance, i.e. the plants are capable of metabolizing the active compounds more quickly via enzyme complexes, that means the active compounds are degraded more rapidly in the plant). According to the Herbicide Resistance Action Committee (abbreviation: HRAC; a committee of the research-conducting industries), resistances to approved active compounds are classified according to their mode of action (MoA): e.g. HRAC group A=acetylcoenzyme-A carboxylase inhibitors (MoA: ACCase) or HRAC group B=acetolactate synthase inhibitors (MoA: ALS). These improvements of the application profile may be of importance both individually and in combination with one another.

One way of improving the application profile of a herbicide may be to combine the active compound with one or more other suitable active compounds. However, in the combined application of a plurality of active compounds, there are frequently phenomena of chemical, physical and biological incompatibility, for example lack of stability of a coformulation, decomposition of an active compound and/or antagonism of the active compounds. What is desired, however, are combinations of active compounds having a favorable activity profile, high stability and ideally a synergistically enhanced activity which allows the application rate to be reduced compared to the individual application of the active compounds to be combined. Likewise, desirable are combinations of active compounds which increase crop plant compatibility in general and/or can be used for specific production techniques. These include, for example, a reduction of sowing depth which, for crop compatibility reasons, can frequently not be used. In this manner, in general a more rapid emergence of the crop is achieved, their risk of emergence diseases (such as, for example, *Pythium* and *Rhizoctonia*) is reduced, and winter survival and stocking are improved. This also applies to late sowing which would otherwise not be possible owing to the crop compatibility risk.

SUMMARY

It was an object of the present invention to improve the application profile of the herbicidal active compound aclonifen with respect to:

a more simple application method which reduces the costs for the user and would thus be more environmentally compatible.

an improvement and application flexibility of the active compounds from pre-emergence to post-emergence of the crop and weed plants.

an improvement and application flexibility of the reliability of action on soils with different soil properties.

an improvement of the reliability of action to resistant weed plant species which would allow a novel option for an effective resistance management.

an improvement and application flexibility of the reliability of action with different irrigation conditions.

This object was achieved by providing herbicidal compositions comprising aclonifen and the further herbicides pendimethalin and picolinafen.

Accordingly, the invention provides herbicidal compositions comprising, as sole herbicidally active constituents:
A) aclonifen (component A),
B) pendimethalin (component B) and
C) picolinafen (component C).

DETAILED DESCRIPTION OF A PREFERRED EMBODIMENT

The active compounds (herbicidally active constituents) referred to in the present description by their common names are known, for example, from "The Pesticide Manual", 15. edition 2009, or from the corresponding "The e-Pesticide Manual", version 5.2 (2008-2011), each published by the BCPC (British Crop Protection Council), and from "The Compendium of Pesticide Common Names" on the Internet (website: http://www.alanwood.net/pesticides/).

Together, the herbicidally active constituents component A, B and C are hereinbelow referred to as "(individual) active compounds", "(individual) herbicides" or as "herbicide components", and they are known, as individual compounds or as mixture, for example from "The Pesticide Manual", 15. edition (see above), where they have the following entry numbers (abbreviation: "PM #." with the respective sequential entry number):

component A: aclonifen (PM #10), e.g. 2-chloro-6-nitro-3-phenoxybenzenamine;
component B: pendimethalin (PM #660), e.g. N-(1-ethylpropyl)-3,4-dimethyl-2,6-dinitrobenzenamine;
component C: picolinafen (PM #685), e.g. N-(4-fluorophenyl)-6-[3-(trifluoromethyl)phenoxy]-2-pyridinecarboxamide.

If the short form of the common name of an active ingredient is used in the context of this description, this—if applicable—therefore refers in each case to all common derivatives, such as the esters and salts, and isomers, especially optical isomers, more particularly the commercial form or forms. If an ester or salt is referred to by the common name, this therefore also refers in each case to all other common derivatives, such as other esters and salts, the free acids and neutral compounds, and isomers, especially optical isomers, especially the commercial form or forms. The stated chemical compound names identify at least one of the compounds embraced by the common name, frequently a preferred compound.

If the abbreviation "AS/ha" is used in the present description, it means "active substance per hectare", based on 100% active compound. All percentages in the description are percent by weight (abbreviation: "% by weight") and, unless defined otherwise, refer to the relative weight of the respective component based on the total weight of the herbicidal composition (for example as formulation).

The herbicidal compositions according to the invention comprise a herbicidally effective amount of components A, B and C and may comprise further constituents, for example agrochemically active compounds from the group of the insecticides, fungicides and safeners, and/or formulation auxiliaries and/or additives customary in crop protection, or be used together with these.

In a preferred embodiment, the herbicidal compositions according to the invention have, as an improvement of the application profile, synergistic effects. These synergistic effects can be observed, for example, when applying the herbicide components together; however, they can frequently also be observed when the components are applied at different times (splitting). It is also possible to apply the individual herbicides or the herbicide combinations in a plurality of portions (sequential application), for example pre-emergence applications followed by post-emergence applications or early post-emergence applications followed by medium or late post-emergence applications. Preference is given here to the joint or almost simultaneous application of the active compounds of the herbicidal compositions according to the invention.

The synergistic effects permit a reduction of the application rates of the individual active compounds, a higher efficacy at the same application rate, the control of species which are as yet uncovered (gaps), an extension of the period of application and/or a reduction in the number of individual applications required and—as a result for the user—weed control systems which are more advantageous economically and ecologically.

The application rate of the herbicide components and their derivatives in the herbicidal composition may vary within wide ranges. Applied at application rates of from 511 to 8500 g of AS/ha by the pre- and post-emergence method, the herbicide components control a relatively broad spectrum of annual and perennial broad-leaved weeds, weed grasses and Cyperaceae.

The application rates of the herbicide components in the herbicidal composition, with respect to one another, are present in the weight ratio stated below:
(range component A):(range component B):(range component C)
generally (1-100):(1-100):(0.1-100),
preferably (1-25):(1-25):(0.5-50),
particularly preferably (1-10):(1-10):(1-10).

The application rates of the respective herbicide components in the herbicidal composition are:
component A: generally 10-5000 g of AS/ha, preferably 80-3000 g of AS/ha, particularly preferably 80-1000 g of AS/ha of aclonifen;
component B: generally 500-3000 g of AS/ha, preferably 500-2500 g of AS/ha, particularly preferably 500-1200 g of AS/ha of pendimethalin;
component C: generally 1-500 g of AS/ha, preferably 10-300 g of AS/ha, particularly preferably 30-200 g of AS/ha of picolinafen.

Correspondingly, the application rates mentioned above may be used to calculate the percentages by weight (% by weight) of the herbicide components based on the total weight of the herbicidal compositions, which may additionally also comprise other components.

The herbicidal compositions according to the invention have excellent herbicidal activity against a broad spectrum of economically important monocotyledonous and dicotyledonous harmful plants, such as broad-leaved weeds, weed grasses or Cyperaceae, including species which are resistant to herbicidal active compounds such as glyphosate, glufosinate, atrazine, photosynthesis inhibitors, imidazolinone herbicides, sulfonylureas, (hetero)aryloxyaryloxyalkylcarboxylic acids or phenoxyalkylcarboxylic acids ('fops'), cyclohexanedione oximes ('dims') or auxin inhibitors. The active compounds also act efficiently on perennial weeds which produce shoots from rhizomes, root stocks and other perennial organs and which are difficult to control. Here, the substances can be applied, for example, by the pre-sowing method, the pre-emergence method or the post-emergence method, for example jointly or separately.

Specific examples of some representatives of the monocotyledonous and dicotyledonous weed flora which can be controlled by the herbicidal compositions according to the invention are as follows, though the enumeration is not intended to impose a restriction to particular species.

Examples of weed species on which the herbicidal compositions act efficiently are, from amongst the monocotyledonous weed species, *Avena* spp., *Alopecurus* spp., *Apera* spp., *Brachiaria* spp., *Bromus* spp., *Digitaria* spp., *Lolium* spp., *Echinochloa* spp., *Leptochloa* spp., *Fimbristylis* spp., *Panicum* spp., *Phalaris* spp., Poa spp., *Setaria* spp. and also *Cyperus* species from the annual group, and, among the perennial species, *Agropyron, Cynodon, Imperata* and *Sorghum* and also perennial *Cyperus* species.

In the case of the dicotyledonous weed species, the spectrum of action extends to genera such as, for example, *Abutilon* spp., *Amaranthus* spp., *Chenopodium* spp., *Chrysanthemum* spp., Galium spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp., *Eclipta* spp., *Sesbania* spp., *Aeschynomene* spp. and *Viola* spp., *Xanthium* spp., among the annuals, and *Convolvulus, Cirsium, Rumex* and *Artemisia* in the case of the perennial weeds.

If the inventive herbicidal compositions are applied to the soil surface before germination, either the weed seedlings are prevented completely from emerging or the weeds grow until they have reached the cotyledon stage, but then stop growing, and eventually, after two to four weeks have elapsed, die completely.

If the herbicidal compositions according to the invention are applied post-emergence to the green parts of the plants, growth likewise stops drastically a very short time after the treatment, and the weed plants remain in the growth stage at the point of time of application, or they die completely after a certain time, so that in this manner competition by the weeds, which is harmful to the crop plants, is eliminated very early and in a sustained manner. In the case of rice, the herbicidal compositions according to the invention can also be applied into the water, and they are then taken up via soil, shoot and roots.

The herbicidal compositions according to the invention are distinguished by a rapidly commencing and long-lasting herbicidal action. In general, the rainfastness of the active compounds in the compositions according to the invention is favorable. A particular advantage is that the dosages used in the compositions according to the invention and the effective dosages of components A, B and C can be adjusted to such a low level that their soil action is optimally low. This does not only allow them to be employed in sensitive crops in the first place, but ground water contaminations are also virtually avoided. The combination according to the invention of active compounds allows the necessary application rate of the active compounds to be reduced considerably.

When the components A, B and C are applied jointly in the compositions according to the invention, there are, in a preferred embodiment, as improvement of the application profile, superadditive (=synergistic) effects. Here, the activity in the combinations is higher than the expected sum of the activities of the individual herbicides employed. The synergistic effects allow higher efficacy and/or longer persistency; the control of a wider spectrum of broad-leaved weeds, weed grasses and Cyperaceae, in some cases with only one or a few applications; a more rapid onset of the herbicidal action; the control of species which are as yet uncovered (gaps); the control of, for example, species which are tolerant or resistant to individual herbicides or to a number of herbicides; an extension of the period of application and/or a reduction in the number of individual applications required or a reduction of the total application rate and—as a result for the user—weed control systems which are more advantageous economically and ecologically.

The abovementioned properties and advantages are necessary for practical weed control to keep agricultural/forestry/horticultural crops, green land/meadows or crops for generating energy (biogas, bioethanol) free of unwanted competing plants, and thus to ensure and/or increase yield levels from the qualitative and quantitative angle. These novel combinations in the herbicidal compositions according to the invention markedly exceed the technical state of the art with a view to the properties described.

Even though the herbicidal compositions according to the invention have an outstanding herbicidal activity toward mono- and dicotyledonous harmful plants, the crop plants are damaged only to a minor degree, if at all.

Furthermore, some of the compositions according to the invention can have growth-regulating properties with respect to the crop plants. They intervene in the plants' own metabolism with regulatory effect, and can thus be used for the targeted influencing of plant ingredients and to facilitate harvesting, such as e.g. by triggering desiccation and stunted growth. Furthermore, they are also suitable for the general control and inhibition of unwanted vegetative growth without killing the plants in the process Inhibition of vegetative growth is very important for many mono- and dicotyledonous crops, since this can reduce or completely prevent harvesting losses caused by lodging.

Owing to their improved application profile, the compositions according to the invention can also be employed for controlling harmful plants in known plant crops or in tolerant or genetically modified crop and energy plants still to be developed. In general, transgenic plants (GMOs) are characterized by particular advantageous properties, for example by resistances to certain pesticides, in particular certain herbicides (such as resistances against components A, B and C in the compositions according to the invention), for example by resistances to harmful insects, plant diseases or pathogens of plant diseases, such as certain microorganisms such as fungi, bacteria or viruses. Other specific characteristics relate, for example, to the harvested material with regard to quantity, quality, storability, and the composition of specific constituents. Thus, transgenic plants are known whose starch content is increased, or whose starch quality is altered, or those where the harvested material has a different fatty acid composition, or increased vitamin content or energetic properties. Further special properties may be tolerance or resistance to abiotic stress factors, for example heat, cold, drought, salinity and ultraviolet radiation. In the same manner, owing to their herbicidal and other properties, the compositions according to the invention can also be used for controlling harmful plants in crops of known plants or plants still to be developed by mutant selection, and also crossbreeds of mutagenic and transgenic plants.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044 A, EP 0131624 A). For example, in several cases the following have been described: genetic modifications of crop plants for the purpose of modifying the starch synthesized in the plants (for example WO 92/011376 A, WO 92/014827 A, WO 91/019806 A); transgenic crop plants which are resistant to certain herbicides of the glufosinate type (cf., for example, EP 0242236 A, EP 0242246 A) or glyphosate (WO 92/000377 A) or of the sulfonylurea type (EP 0257993 A, U.S. Pat. No. 5,013,659) or to combinations or mixtures of these herbicides through "gene stacking", such as transgenic crop plants e.g. corn or soybean with the tradename or the name Optimum™ GAT™ (glyphosate ALS tolerant); transgenic crop plants, for example cotton, with the capability of producing *Bacillus thuringiensis* toxins (Bt toxins) which make the plants resistant to certain pests (EP 0142924 A, EP 0193259 A); transgenic crop plants having a modified fatty acid composition (WO 91/013972 A); genetically modified crop plants having novel constituents or secondary compounds, for example novel phytoalexins providing increased resistance to disease (EP 0309862 A, EP 0464461 A); genetically modified plants having reduced photorespiration, which provide higher yields and have higher stress tolerance (EP 0305398 A); transgenic crop plants producing pharmaceutically or diagnostically important proteins ("molecular pharming"); transgenic crop plants distinguished by higher yields or better quality; transgenic crop plants distinguished by a combination, for example of the novel properties mentioned above ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431. To carry out such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is possible firstly to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or expression of heterologous (=foreign) genes or gene sequences.

The present invention furthermore also provides a method for the control of unwanted vegetation (for example harmful plants), preferably in crop plants such as cereals (for example durum wheat and common wheat, barley, rye, oats, crossbreeds thereof such as triticale, planted or sown rice under 'upland' or 'paddy' conditions, corn, millet such as, for example, sorghum, sugar beet, sugar cane, oilseed rape, cotton, sunflowers, soybeans, potatoes, tomatoes, beans such as, for example, bush beans and broad beans, flax, pasture grass, fruit plantations, plantation crops, greens and lawns, and also squares of residential areas or industrial sites, rail tracks, particularly preferably in monocotyledonous crops such as cereals, for example wheat, barley, rye, oats, crossbreeds thereof such as triticale, rice, corn and millet and also dicotyledonous crops such as sunflowers, soybeans, potatoes, tomatoes, peas, carrots and fennel where the components A, B and C of the herbicidal compositions according to the invention are applied to the plants, for example harmful plants, plant parts, plant seeds or the area on which the plants grow, for example the area under cultivation, jointly or separately, for example by the pre-emergence method (very early to late), post-emergence method or pre-emergence and post-emergence.

The invention also provides the use of the herbicidal compositions according to the invention comprising the components A, B and C for the control of harmful plants, preferably in crop plants, preferably in the crop plants mentioned above. Furthermore, the invention also provides the use of the herbicidal compositions according to the invention comprising the components A, B and C for the control of herbicide-resistant harmful plants (for example TSR and EMR resistances in the case of ALS and ACCase), preferably in crop plants, preferably in the crop plants mentioned above.

The invention also provides the method with the herbicidal compositions according to the invention comprising the components A, B and C for the selective control of harmful plants in crop plants, preferably in the crop plants mentioned above, and its use.

The invention also provides the method for controlling unwanted vegetation with the herbicidal compositions according to the invention comprising the components A, B and C, and its use in crop plants which have been modified by genetic engineering (transgenic) or obtained by mutation selection, and which are resistant to growth regulators such as, for example, 2,4 D, dicamba, or against herbicides which inhibit essential plant enzymes, for example acetolactate synthases (ALS), EPSP synthases, glutamine synthases (GS) or hydroxyphenylpyruvate dioxygenases (HPPD), or respectively to herbicides from the group of the sulfonylureas, glyphosates, glufosinates or benzoylisoxazoles and analogous active compounds, or to any combinations of these active compounds. The herbicidal compositions according to the invention can be used with particular preference in transgenic crop plants which are resistant to a combination of glyphosates and glufosinates, glyphosates and sulfonylureas or imidazolinones. Very particularly preferably, the herbicidal compositions according to the invention can be used in transgenic crop plants such as, for example, corn or soybean with the tradename or the name Optimum™ GAT™ (glyphosate ALS tolerant).

The invention also provides the use of the herbicidal compositions according to the invention comprising the components A, B and C for the control of harmful plants, preferably in crop plants, preferably in the crop plants mentioned above.

The herbicidal compositions according to the invention can also be used non-selectively for controlling unwanted vegetation, for example in plantation crops, at the wayside, on squares, industrial sites or railway installations; or selectively for controlling unwanted vegetation in crops for energy generation (biogas, bioethanol).

The herbicidal compositions according to the invention can be present both as mixed formulations of components A, B and C and, if appropriate, with further agrochemical active compounds, additives and/or customary formulation auxiliaries which are then applied in a customary manner diluted with water, or can be prepared as so-called tank mixes by joint dilution of the separately formulated or partially separately formulated components with water. In certain cases, the mixed formulations can be diluted with other liquids or solids, or else be applied in undiluted form.

The components A, B and C or their subcombinations can be formulated in various ways, depending on the prevailing biological and/or chemico-physical parameters. Examples of general formulation options are: wettable powders (WP), water-soluble concentrates, emulsifiable concentrates (EC), aqueous solutions (SL), emulsions (EW), such as oil-in-water and water-in-oil emulsions, sprayable solutions or emulsions, suspension concentrates (SC), dispersions, oil dispersions (OD), suspoemulsions (SE), dusts (DP), seed-dressing products, granules for soil application or spreading (GR) or water-dispersible granules (WG), ultra-low volume formulations, microcapsule dispersions or wax dispersions.

The individual types of formulation are known in principle and are described, for example, in: "Manual on Development and Use of FAO and WHO Specifications for Pesticides", FAO and WHO, Rome, Italy, 2002; Winnacker-Küchler, "Chemische Technologie" [Chemical Technology], Volume 7, C. Hanser Verlag Munich, 4th ed. 1986; van Valkenburg, "Pesticide Formulations", Marcel Dekker N.Y. 1973; K. Martens, "Spray Drying Handbook", 3rd ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry"; 2nd ed., J. Wiley & Sons, N.Y.; Marsden, "Solvents Guide", 2nd ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Technology], volume 7, C. Hanser Verlag Munich, 4th ed. 1986.

Based on these formulations, it is also possible to prepare combinations with other agrochemical active compounds such as fungicides, insecticides and also safeners, fertilizers and/or growth regulators, for example in the form of a readymix or as tank mix.

Wettable powders (sprayable powders) are products which are uniformly dispersible in water and which, besides the active compounds and in addition to one or more diluents or inert substances, also comprise ionic and/or nonionic surfactants (wetting agents, dispersants), for example polyoxyethylated alkylphenols, polyethoxylated fatty alcohols or fatty amines, propylene oxide/ethylene oxide copolymers, alkanesulfonates or alkylbenzenesulfonates or alkylnaphthalenesulfonates, sodium lignosulfonate, sodium 2,2'-dinaphthylmethane-6,6'-disulfonate, sodium dibutylnaphthalenesulfonate or else sodium oleoylmethyltauride.

Emulsifiable concentrates are prepared by dissolving the active compounds in an organic solvent or solvent mixture, for example butanol, cyclohexanone, dimethylformamide, acetophenone, xylene or else higher-boiling aromatics or hydrocarbons with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide copolymers, alkyl polyethers, sorbitan fatty acid esters, polyoxyethylene sorbitan fatty acid esters or polyoxyethylene sorbitol esters.

Dustable powders are obtained by grinding the active compound with finely distributed solid substances, for example talc, natural clays such as kaolin, bentonite and pyrophyllite, or diatomaceous earth.

Suspension concentrates are water-based suspensions of active compounds. They may be prepared, for example, by wet grinding by means of commercially available bead mills and optional addition of further surfactants as have, for example, already been listed above for the other formulation types. In addition to the suspended active compound or active compounds, other active compounds may also be present in the formulation in dissolved form.

Oil dispersions are oil-based suspensions of active compounds, where oil is to be understood as meaning any organic liquid, for example vegetable oils, aromatic or aliphatic solvents, or fatty acid alkyl esters. They can be prepared, for example, by wet grinding by means of commercially available bead mills and, if appropriate, addition of further surfactants (wetting agents, dispersants) as have already been mentioned, for example, above in the case of the other formulation types. In addition to the suspended active compound or active compounds, other active compounds may also be present in the formulation in dissolved form.

Emulsions, for example oil-in-water emulsions (EW), can be prepared, for example, by means of stirrers, colloid mills and/or static mixers from mixtures of water and water-immiscible organic solvents and, if appropriate, further surfactants as have already been mentioned, for example, above in the case of the other formulation types. Here, the active compounds are present in dissolved form.

Granules can be prepared either by spraying the active compound onto adsorptive, granulated inert material or by applying active compound concentrates to the surface of carriers such as sand, kaolinites, chalk or granulated inert material with the aid of binders, for example polyvinyl alcohol, sodium polyacrylate or else mineral oils. Suitable active compounds can also be granulated in the manner customary for the preparation of fertilizer granules—if desired as a mixture with fertilizers. Water-dispersible granules are produced generally by the customary processes such as spray-drying, fluidized bed granulation, pan granulation, mixing with high-speed mixers and extrusion without solid inert material. For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.;

"Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations generally comprise from 0.1 to 99% by weight, in particular from 2 to 95% by weight, of active compounds of the herbicide components, the following concentrations being customary, depending on the type of formulation: In wettable powders, the active compound concentration is, for example, about 10 to 95% by weight, the remainder to 100% by weight consisting of customary formulation constituents. In the case of emulsifiable concentrates, the active compound concentration can be, for example, from 5 to 80% by weight. In most cases, formulations in the form of dusts comprise from 5 to 20% by weight of active compound, sprayable solutions comprise about 0.2 to 25% by weight of active compound. In the case of granules such as dispersible granules, the active compound content depends partially on whether the active compound is present in liquid or solid form and on which granulation auxiliaries and fillers are used. In water-dispersible granules, the content is generally between 10 and 90% by weight. In addition, the active compound formulations mentioned optionally comprise the respective customary adhesives, wetting agents, dispersants, emulsifiers, preservatives, antifreeze agents and solvents, fillers, colorants and carriers, antifoams, evaporation inhibitors and pH- or viscosity-modifying agents.

The herbicidal action of the herbicide combinations according to the invention can be improved, for example, by surfactants, for example by wetting agents from the group of the fatty alcohol polyglycol ethers. The fatty alcohol polyglycol ethers preferably comprise 10-18 carbon atoms in the fatty alcohol radical and 2-20 ethylene oxide units in the polyglycol ether moiety. The fatty alcohol polyglycol ethers may be present in nonionic form, or ionic form, for example in the form of fatty alcohol polyglycol ether sulfates or phosphates, which are used, for example, as alkali metal salts (for example sodium salts and potassium salts) or ammonium salts, or even as alkaline earth metal salts, such as magnesium salts, such as $C_{12}/C_{14}$-fatty alcohol diglycol ether sulfate sodium (Genapol® LRO, Clariant GmbH); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, $(C_{10}\text{-}C_{18})$-, preferably $(C_{10}\text{-}C_{14})$-fatty alcohol polyglycol ethers (for example isotridecyl alcohol polyglycol ethers) which comprise, for example, 2-20, preferably 3-15, ethylene oxide units, for example from the Genapol® X series, such as Genapol® X-030, Genapol® X-060, Genapol® X-080 or Genapol® X-150 (all from Clariant GmbH).

The present invention further comprises the combination of components A, B and C with the wetting agents mentioned above from the group of the fatty alcohol polyglycol ethers which preferably contain 10-18 carbon atoms in the fatty alcohol radical and 2-20 ethylene oxide units in the polyglycol ether moiety and which may be present in nonionic or ionic form (for example as fatty alcohol polyglycol ether sulfates). Preference is given to sodium $C_{12}/C_{14}$-fatty alcohol diglycol ether sulfate (Genapol® LRO, Clariant GmbH) and isotridecyl alcohol polyglycol ethers having 3-15 ethylene oxide units, for example from the Genapol® X series, such as Genapol® X-030, Genapol® X-060, Genapol® X-080 and Genapol® X-150 (all from Clariant GmbH). It is also known that fatty alcohol polyglycol ethers, such as nonionic or ionic fatty alcohol polyglycol ethers (for example fatty alcohol polyglycol ether sulfates) are also suitable as penetrants and activity enhancers for a number of other herbicides, including herbicides from the group of the imidazolinones (see, for example, EP-A-0502014).

The herbicidal action of the herbicide combinations according to the invention can also be enhanced by using vegetable oils. The term vegetable oils is to be understood as meaning oils of oleaginous plant species, such as soybean oil, rapeseed oil, corn oil, sunflower oil, cottonseed oil, linseed oil, coconut oil, palm oil, thistle oil or castor oil, in particular rapeseed oil, and also their transesterification products, for example alkyl esters, such as rapeseed oil methyl ester or rapeseed oil ethyl ester.

The vegetable oils are preferably esters of $C_{10}\text{-}C_{22}$-, preferably $C_{12}\text{-}C_{20}$-, fatty acids. The $C_{10}\text{-}C_{22}$-fatty acid esters are, for example, esters of unsaturated or saturated $C_{10}\text{-}C_{22}$-fatty acids having, in particular, an even number of carbon atoms, for example erucic acid, lauric acid, palmitic acid and in particular $C_{18}$-fatty acids such as stearic acid, oleic acid, linoleic acid or linolenic acid.

Examples of $C_{10}\text{-}C_{22}$-fatty acid esters are esters which are obtained by reacting glycerol or glycol with the $C_{10}\text{-}C_{22}$-fatty acids present, for example, in oils of oleaginous plant species, or $C_1\text{-}C_{20}$-alkyl $C_{10}\text{-}C_{22}$-fatty acid esters which can be obtained, for example, by transesterification of the glycerol or glycol $C_{10}\text{-}C_{22}$-fatty acid esters mentioned above with $C_1\text{-}C_{20}$-alcohols (for example methanol, ethanol, propanol or butanol). The transesterification can be carried out by known methods as described, for example, in Rompp Chemie Lexikon, 9th edition, volume 2, page 1343, Thieme Verlag Stuttgart.

Preferred $C_1\text{-}C_{20}$-alkyl-$C_{10}\text{-}C_{22}$-fatty acid esters are methyl esters, ethyl esters, propyl esters, butyl esters, 2-ethylhexyl esters and dodecyl esters. Preferred glycol and glycerol $C_{10}\text{-}C_{22}$-fatty acid esters are the uniform or mixed glycol esters and glycerol esters of $C_{10}\text{-}C_{22}$-fatty acids, in particular fatty acids having an even number of carbon atoms, for example erucic acid, lauric acid, palmitic acid and in particular $C_{18}$-fatty acids such as stearic acid, oleic acid, linoleic acid or linolenic acid.

In the herbicidal compositions according to the invention, the vegetable oils can be present, for example, in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), RakoBinol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

In a further embodiment, the present invention embraces combinations of the components A, B and C with the vegetable oils mentioned above, such as rapeseed oil, preferably in the form of commercially available oil-containing formulation additives, in particular those based on rapeseed oil, such as Hasten®, Actirob®B, Rako-Binol®, Renol® or Stefes Mero®.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable formulations are not normally diluted further with other inert substances prior to application.

The active compounds can be applied to the plants, plant parts, seeds or area under cultivation (soil), preferably on the green plants and plant parts, and optionally additionally to the soil.

One means of application is the co-deployment of the active compounds in the form of tank-mixes, by mixing the optimally formulated concentrated formulations of the individual active compounds together in the tank with water and deploying the spray liquor obtained.

A joint herbicidal formulation of the herbicidal compositions according to the invention comprising the components A, B and C has the advantage that it can be applied more easily since the quantities of the components are already adjusted to the correct ratio to one another. Moreover, the auxiliaries in the formulation can be optimized to one another.

A. General Formulation Examples a) A dust is obtained by mixing 10 parts by weight of an active compound/active compound mixture and 90 parts by weight of talc as inert substance and comminuting the mixture in a hammer mill.

b) A wettable powder which is readily dispersible in water is obtained by mixing 25 parts by weight of an active compound/active compound mixture, 64 parts by weight of kaolin-containing clay as inert substance, 10 parts by weight of potassium lignosulphonate and 1 part by weight of sodium oleoylmethyltaurinate as wetting agent and dispersant, and grinding the mixture in a pinned-disk mill.

c) A suspension concentrate which is readily dispersible in water is obtained by mixing 20 parts by weight of an active compound/active compound mixture with 5 parts by weight of tristyrylphenol polyglycol ether (Soprophor BSU), 1 part by weight of sodium lignosulfonate (Vanisperse CB) and 74 parts by weight of water, and grinding the mixture in a ball mill to a fineness of below 5 microns.

d) An oil dispersion which is readily dispersible in water is obtained by mixing 20 parts by weight of an active compound/active compound mixture with 6 parts by weight of alkylphenol polyglycol ether (Triton® X 207), 3 parts by weight of isotridecanol polyglycol ether (8 EO) and 71 parts by weight of paraffinic mineral oil (boiling range for example approx. 255 to 277° C.), and grinding the mixture in a ball mill to a fineness of below 5 microns.

e) An emulsifiable concentrate is obtained from 15 parts by weight of an active compound/active compound mixture, 75 parts by weight of cyclohexanone as solvent and 10 parts by weight of oxyethylated nonylphenol as emulsifier.

f) Water-dispersible granules are obtained by mixing
   75 parts by weight of an active compound/active compound mixture,
   10 parts by weight of calcium lignosulfonate,
   5 parts by weight of sodium laurylsulfate,
   3 parts by weight of polyvinyl alcohol and
   7 parts by weight of kaolin,
   grinding the mixture in a pinned-disk mill, and granulating the powder in a fluidized bed by spray application of water as a granulating liquid.

g) Water-dispersible granules are also obtained by homogenizing and precomminuting, in a colloid mill,
   25 parts by weight of an active compound/active compound mixture,
   5 parts by weight of sodium 2,2'-dinaphthylmethane-6,6'-disulfonate,
   2 parts by weight of sodium oleoylmethyltaurate,
   1 part by weight of polyvinyl alcohol,
   17 parts by weight of calcium carbonate and
   50 parts by weight of water
   then grinding the mixture in a bead mill and atomizing and drying the resulting suspension in a spray tower by means of a one-phase nozzle.

B. Biological Examples a) Description of the Methods

Greenhouse Trials

In the standard design of the test, seeds of various broad-leaved weed and weed grass biotypes (origins) were sown in a 8-13 cm diameter pot filled with natural soil of a standard field soil (loamy silt; non-sterile) and covered with a covering soil layer of about 1 cm. The pots were then cultivated in a greenhouse (12-16 h light, temperature day 20-22° C., night 15-18° C.) until the time of application. The pots were treated on a laboratory track sprayer with spray liquors comprising the compositions according to the invention, mixtures of the prior art or components used individually. Application of the active compounds or active compound combinations formulated as WG, WP, EC or otherwise was carried out at the appropriate growth stages of the plants. The amount of water used for spray application was 100-600 l/ha. After the treatment, the plants were returned to the greenhouses.

About 3 weeks after the application, the soil action or/and foliar action was assessed visually according to a scale of 0-100% in comparison to an untreated comparative group: 0%=no noticeable effect compared to the untreated comparative group; 100%=full effect compared to the untreated comparative group.

(Notes: the term "seeds" also includes vegetative propagation forms such as, for example, rhizome pieces; abbreviations used: h light=hours of illumination, g of AS/ha=grams of active substance per hectare, l/ha=liter per hectare, S=sensitive, R=resistant)

1. Pre-emergence action against weeds: seeds of various broad-leaved weed and weed grass biotypes (origins) were sown in a 8-13 cm diameter pot filled with natural soil of a standard field soil (loamy silt; non-sterile) and covered with a covering soil layer of about 1 cm. The pots were then cultivated in a greenhouse (12-16 h light, temperature day 20-22° C., night 15-18° C.) until the time of application. The pots were treated at BBCH stage 00-10 of the seeds/plants on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required.

2. Post-emergence action against weeds: seeds of various broad-leaved weed and weed grass biotypes (origins) were sown in a 8-13 cm diameter pot filled with natural soil of a standard field soil (loamy silt; non-sterile) and covered with a covering soil layer of about 1 cm. The pots were then cultivated in a greenhouse (12-16 h of light, temperature day 20-22° C., night 15-18° C.) until the time of application. The pots were treated at various BBCH stages between 11-25 of the seeds/plants, i.e. generally between two to three weeks after the start of the cultivation, on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required.

3. Selective pre-emergence action: seeds of various crop species (origins) were sown in a 8-13 cm diameter pot filled with natural soil of a standard field soil (loamy silt; non-sterile) and covered with a covering soil layer of about 1 cm. The pots were then cultivated in a greenhouse (12-16 h light, temperature day 20-22° C., night 15-18° C.) until the time of application. The pots were treated at BBCH stage 00-10 of the seeds/plants on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required.

4. Selective post-emergence action: seeds of various crop species (origins) were sown in a 8-13 cm diameter pot filled with natural soil of a standard field soil (loamy silt; non-sterile) and covered with a covering soil layer of about 1 cm. The pots were then cultivated in a greenhouse (12-16 h light, temperature day 20-22° C., night 15-18° C.) until the time of application. The pots were treated at various BBCH stages 11-32 of the seeds/plants, i.e. generally between two to four weeks after the start of the cultivation, on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required. The pots were cultivated in a greenhouse (12-16 h light, temperature day 20-22° C., night 15-18° C.).

5. Pre-emergence and post-emergence action against weeds under various cultivation conditions: seeds of various broad-leaved weed and weed grass biotypes (origins) were sown in a 8-13 cm diameter pot filled with natural soil of a standard field soil (loamy silt; non-sterile) and covered with a covering soil layer of about 1 cm. The pots were then cultivated in a greenhouse (12-16 h light, temperature day 20-22° C., night 15-18° C.) until the time of application. The pots were treated at various BBCH stages 00-25 of the seeds/plants on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required. The pots were cultivated in a greenhouse (12-16 h light, temperature day 20-22° C., night 15-18° C.). Irrigation was varied according to the issue. Here, the individual comparative groups were provided with gradually differing amounts of water in a range from above the PWP (permanent wilting point) up to the level of maximum field capacity.

6. Pre-emergence and post-emergence action against weeds under various irrigation conditions: seeds of various broad-leaved weed and weed grass biotypes (origins) were sown in a 8-13 cm diameter pot filled with natural soil of a standard field soil (loamy silt; non-sterile) and covered with a covering soil layer of about 1 cm. The pots were then cultivated in a greenhouse (12-16 h light, temperature day 20-22° C., night 15-18° C.) until the time of application. The pots were treated at various BBCH stages 00-25 of the seeds/plants on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required. The pots were cultivated in a greenhouse (12-16 h light, temperature day 20-22° C., night 15-18° C.). The individual comparative groups were subjected to different irrigation techniques. Irrigation was either from below or gradually from above (simulated rain).

7. Pre-emergence and post-emergence action against weeds under various soil conditions: seeds of various broad-leaved weed and weed grass biotypes (origins) were sown in a 8-13 cm diameter pot filled with natural soil and covered with a covering soil layer of about 1 cm. To compare the herbicidal action, the plants were cultivated in various cultivation soils from sandy soil to heavy clay soil and various contents of organic substance. The pots were then cultivated in a greenhouse (12-16 h light, temperature day 20-22° C., night 15-18° C.) until the time of application. The pots were treated at various BBCH stages 00-25 of the seeds/plants on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required. The pots were cultivated in a greenhouse (12-16 h light, temperature day 20-22° C., night 15-18° C.).

8. Pre-emergence and post-emergence action against weeds for the control of resistant weed grass/broad-leaved weed species: seeds of various broad-leaved weed and weed grass biotypes (origins) having various resistance mechanisms against different modes of action were sown in a 8-13 cm diameter pot filled with natural soil of a standard field soil (loamy silt; non-sterile) and covered with a covering soil layer of about 1 cm. The pots were then cultivated in a greenhouse (12-16 h light, temperature day 20-22° C., night 15-18° C.) until the time of application. The pots were treated at various BBCH stages 00-25 of the seeds/plants on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required. The pots were cultivated in a greenhouse (12-16 h light, temperature day 20-22° C., night 15-18° C.).

9. Pre-emergence and post-emergence action against weeds and crop selectivity under various sowing conditions: seeds of various broad-leaved weed and weed grass biotypes (origins) and crop species (origins) were sown in a 8-13 cm diameter pot filled with natural soil and covered with a covering soil layer of about 0-5 cm. The pots were then cultivated in a greenhouse (12-16 h light, temperature day 20-22° C., night 15-18° C.) until the time of application. The pots were treated at various BBCH stages 00-25 of the seeds/plants on a laboratory track sprayer with spray liquors comprising the compositions according to the invention, mixtures or the components applied individually as WG, WP, EC or other formulations. The amount of water used for spray application was 100-600 l/ha. After the treatment, the plants were returned to the greenhouses and fertilized and watered as required. The pots were cultivated in a greenhouse (12-16 h light, temperature day 20-22° C., night 15-18° C.).

Outdoor Trials

In outdoor trials under natural conditions with the field being prepared in a manner customary in practice and with natural or artificial infestation with harmful plants, the compositions according to the invention, mixtures of the prior art or the individual components were applied before or after sowing of the crop plants or before or after emergence of the harmful plants, and visual scoring was carried out over a period of 4 weeks to 8 months after the treatment by comparison with untreated sections (plots). Here the damages to the crop plants and the action against harmful plants were recorded in percent, like the other effects of the respective trial question.

b) Results

The following abbreviations were used:

BBCH=the BBCH code provides information about the morphological development stage of a plant. Officially, the abbreviation denotes the Biologische Bundesanstalt, Bundessortenamt and Chemische Industrie [Federal Biological Institute for Agriculture and Forestry, Federal Office for Crop Plant Varieties, Chemical Industry]. The range of BBCH 00-10 denotes the germination stages of the seeds until surface penetration. The range of BBCH 11-25 denotes the leaf development stages until stocking (corresponding to the number of tillers or side-shoots).

PE=pre-emergence application on the soil; BBCH of the seeds/plants 00-10.

PO=post-emergence application on the green parts of the plants; BBCH of the plants 11-25.

HRAC=Herbicide Resistance Action Committee which classifies the approved active compounds according to their mode of action (MoA).

HRAC group A=acetyl coenzyme A carboxylase inhibitors (MoA: ACCase).

HRAC group B=acetolactate synthase inhibitors (MoA: ALS).

AS=active substance (based on 100% of active ingredient; syn. a.i.).

Dosage g of AS/ha=application rate in grams of active substance per hectare.

The names used for the respective ryegrass biotypes in the results are the botanical names, among others *Lolium* spp. (LOLSS), *Lolium multiflorum* (LOLMU), *Lolium perenne* (LOLPE) (in brackets: EPPO code or former Bayer code).

The activities of the herbicidal compositions according to the invention meet the stated requirements and therefore solve the object of improving the application profile of the herbicidal active compound aclonifen (inter alia provision of more flexible solutions with regard to the application rates required for unchanged to enhanced activity).

Insofar as herbicidal effects of the compositions according to the invention compared to mixtures of the prior art or compared to components applied individually against economically important mono- and dicotyledonous harmful plants were the center of attention, the synergistic herbicidal activities were calculated using Colby's formula (cf. S. R. Colby; Weeds 15 (1967), 20-22):

$$E^C = (A+B+C) - (A \times B + A \times C + B \times C)/100 + (A \times B \times C)/10000$$

where:

A, B, C=the activity of components A, B and C, respectively, in percent at a rate of a, b and c grams of AS/ha, respectively;

$E^C$=expected value according to Colby in % at a rate of a+b+c grams of AS/ha.

$\Delta$=difference (%) of the measured value (%) to the expected value (%) (measured value minus expected value).

Evaluation:—measured values: in each case for (A), (B) and (C) and (A)+(B)+(C) in %.

Assessment:—measured value (%) greater > than $E^C$: ≙ synergism (+$\Delta$).

measured value (%) equal to =$E^C$: ≙ additive effect (±0$\Delta$).

measured value (%) smaller < than $E^C$: ≙ antagonism (−$\Delta$).

TABLE 1

Comparison of the effect of the mixture on various ryegrass biotypes - greenhouse experiment; post-emergence treatment (PO, BBCH 11).

| | Dose g of AS/ha | *Lolium* spp. resistant to HRAC group A | *Lolium* spp. resistant to HRAC group B |
|---|---|---|---|
| (A) aclonifen | 225 | 25 | 50 |
| (B) pendimethalin | 300 | 5 | 0 |
| (C) picolinafen | 25 | 10 | 5 |
| (A) + (B) + (C) calculation according to Colby | 225 + 300 + 25 | 50 $E^c = 36$; $\Delta + 14$ | 80 $E^c = 53$; $\Delta + 27$ |
| pinoxaden + cloquintocet-mexyl[1]; HRAC group A (ACCase) | 60 + 15 | 40 | — |
| mesosulfuron + iodosulfuron + mefenpyr[1]; HRAC group B (ALS) | 15 + 3 + 45 | — | 0 |

Note:
the products BANDUR, STOMP SC and SNIPER were used for aclonifen, pendimethalin and picolinafen, respectively;
[1]comparative product for showing the resistance present in the various biotypes.

For the plant species investigated, a clear synergistic effect against the resistant biotypes of HRAC groups A and B could be demonstrated for the mixture ($\Delta$+14% and $\Delta$+27%, respectively).

The invention claimed is:

1. A herbicidal composition comprising, as sole herbicidally active constituents,
   A) aclonifen (component A),
   B) pendimethalin (component B) and
   C) picolinafen (component C), wherein A, B and C in combination exhibits synergy in comparison to A, B and C individually.

2. The herbicidal composition as claimed in claim 1, wherein the herbicide components are present in the weight ratio:
   (range component A): (range component B): (range component C)
   (1-100):(1-100):(0.1-100).

3. The herbicidal composition as claimed in claim 1, comprising the herbicide components in the application rates of:
   component A: 10-5000 g of AS/ha, of aclonifen;
   component B: 500-3000 g of AS/ha, of pendimethalin;
   component C: 1-500 g of AS/ha, of picolinafen.

4. The herbicidal composition as claimed in claim 1, additionally comprising one or more formulation auxiliaries and/or additives.

5. The herbicidal composition as claimed in claim 1, additionally comprising one or more further components selected from the group of agrochemical active compounds comprising insecticides, fungicides and safeners.

6. A herbicidal composition of claim 1 effective in controlling one or more harmful plants.

7. A herbicidal composition of claim 1 effective in controlling one or more herbicide-resistant harmful plants.

8. The herbicidal composition as claimed in claim 1, wherein the herbicide components are present in the weight ratio of: (range component A): (range component B): (range component C) of (1-10):(1:10): (1-10).

9. The herbicidal composition as claimed in claim 1, wherein the herbicide components are present in the weight ratio of: (range component A): (range component B): (range component C) of (1-25):(1-25):(0.5-50).

10. The herbicidal composition as claimed in claim 1, comprising the herbicide components in the application rates:

component A:80-3000 g of AS/ha of aclonifen;
component B:500-2500 g of AS/ha of pendimethalin;
component C:10-300 g of AS/ha of picolinafen.

11. The herbicidal composition as claimed in claim 1, comprising the herbicide components in the application rates:

component A:80-1000 g of AS/ha of aclonifen;
component B:500-1200 g of AS/ha of pendimethalin;
component C:30-200 g of AS/ha of picolinafen.

12. A method for controlling unwanted vegetation which comprises applying
A) aclonifen (component A),
B) pendimethalin (component B) and
C) picolinafen (component C)
jointly or separately to one or more plants, plant parts, plant seeds and/or an area on which plants grow wherein A, B and C applied in combination exhibits synergy in comparison to A, B and C applied individually.

13. The method as claimed in claim 12 for the selective control of harmful plants in plant crops.

14. The method as claimed in claim 13 in which the plant crops are genetically modified or have been obtained by mutation selection.

15. The method as claimed in claim 12, wherein A, B and C are applied post-emergently.

16. The method as claimed in claim 12, wherein A, B and C are applied pre-emergently.

* * * * *